United States Patent
Fujimoto et al.

(10) Patent No.: US 11,186,610 B2
(45) Date of Patent: Nov. 30, 2021

(54) CRYSTAL OF GLUTATHIONE TRISULFIDE DIHYDRATE AND METHOD FOR PRODUCING SAME

(71) Applicant: KYOWA HAKKO BIO CO., LTD., Tokyo (JP)

(72) Inventors: Akihiro Fujimoto, Tokyo (JP); Hiroshi Nagano, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 16/470,790

(22) PCT Filed: Dec. 20, 2017

(86) PCT No.: PCT/JP2017/045805
§ 371 (c)(1),
(2) Date: Jun. 18, 2019

(87) PCT Pub. No.: WO2018/117186
PCT Pub. Date: Jun. 28, 2018

(65) Prior Publication Data
US 2020/0079818 A1    Mar. 12, 2020

(30) Foreign Application Priority Data
Dec. 20, 2016   (JP) .............................. JP2016-246115

(51) Int. Cl.
*C07K 5/093*     (2006.01)

(52) U.S. Cl.
CPC .................. *C07K 5/0819* (2013.01)

(58) Field of Classification Search
None
See application file for complete search history.

(56) References Cited

U.S. PATENT DOCUMENTS

| | | | |
|---|---|---|---|
| 2013/0035470 A1* | 2/2013 | Kimura .................. | C30B 29/54 530/331 |
| 2016/0272677 A1* | 9/2016 | Bianchi .................. | A61P 39/06 |
| 2018/0094025 A1 | 4/2018 | Ooshima et al. | |

FOREIGN PATENT DOCUMENTS

| | | |
|---|---|---|
| WO | WO 2011/132724 A1 | 10/2011 |
| WO | WO 2015/067708 A1 | 5/2015 |
| WO | WO 2016/159317 A1 | 10/2016 |
| WO | WO 2016159317 | * 10/2016 |

OTHER PUBLICATIONS

Moutiez et al. ("Reduction of a trisulfide derivative of glutathione by glutathione reductase."Biochem. Biophys. Res. Commun., 1994, vol. 202, No. 3, pp. 1380-1386).*

Purdie et al. ("Chromatography of cysteine and glutathione derivatives on a Dowex 1/Sephadex mixed-bed column", J. Chromatogr., 1971, vol. 59, No. 1, pp. 181-184).*

Caira, "Crystalline Polymorphism of Organic Compounds," *Topics in Current Chemistry*, 198: 163-208 (1998).

Atwood et al., "Sulfur: Organic Polysulfanes," *Encyclopedia of Inorganic and Bioinorganic Chemistry*, published by John Wiley & Sons, Ltd., pp. 1-32 (2006).

Kimura et al., "Hydrogen sulfide protects neurons from oxidative stress," *FASEB J.*, 18(10): 1165-1167 (2004).

Massey et al., "The Presence of S°-Containing Impurities in Commercial Samples of Oxidized Glutathione and Their Catalytic Effect on the Reduction of Cytochrome c" *Biochem. Biophys. Res. Commun.*, 42(2): 730-738 (1971).

Moutiez et al., "Reduction of a Trisulfide Derivative of Glutathione by Glutathione Reductase," *Biochem. Biophys. Res. Common.*, 202(3): 1380-1386 (1994).

Purdie et al., "Chromatography of cysteine and glutathione derivatives on a Dowex 1/Sephadex mixed-bed column," *J. Chromatogr.*, 59(1): 181-184 (1971).

Japanese Patent Office, International Search Report in International Patent Application No. PCT/JP2017/045805 (dated Apr. 3, 2018).

Japanese Patent Office, Written Opinion of the International Searching Authority in International Patent Application No. PCT/JP2017/045805 (dated Apr. 3, 2018).

Hamid et al., "Polysulfide stabilization by tyrosine and hydroxyphenyl-containing derivatives that is important for a reactive sulfur metabolomics analysis," *Redox Biol.*, 21: 101096 (2019).

Steudel, "The Chemistry of Organic Polysulfanes $R-S_n-R$ (n > 2)," *Chem. Rev.*, 102(11): 3905-3945 (2002).

Balbach et al., "Pharmaceutical evaluation of early development candidates 'the 100 mg-approach,'" *Int. J. Pharm.*, 275(1-2): 1-12 (2004).

Singhal et al., "Drug polymorphism and dosage form design: a practical perspective," *Adv. Drug Deliv. Rev.*, 56(3): 335-347 (2004).

Australian Patent Office, Examination Report in Australian Patent Application No. 2017380220 (dated Nov. 25, 2020).

Moutiez et al., "Compared recognition of di- and trisulfide substrates by glutathione and trypanothione reductases," *Biochim. Biophys. Acta*, 1245(2): 161-166 (1995).

European Patent Office, Extended European Search Report in European Patent Application No. 17882683.0 (dated Jul. 28, 2020).

* cited by examiner

*Primary Examiner* — Maury A Audet
(74) *Attorney, Agent, or Firm* — Leydig, Voit & Mayer, Ltd.

(57) ABSTRACT

The present invention relates to a crystal of glutathione trisulfide dihydrate and a method for producing the same. According to the present invention, for example, the crystal can be provided by concentrating an aqueous solution in which glutathione trisulfide is dissolved and collecting the precipitated crystal of glutathione trisulfide dihydrate. In addition, the present invention relates to a simple method for producing polysulfide in an aqueous solvent using thiosulfate without using hydrogen sulfide, by stirring an aqueous solution in which a compound having a thiol group or a disulfide bond and thiosulfate are dissolved or by leaving the aqueous solution to stand.

18 Claims, 3 Drawing Sheets

CRYSTAL OF GLUTATHIONE TRISULFIDE DIHYDRATE AND METHOD FOR PRODUCING SAME

CROSS-REFERENCE TO RELATED APPLICATIONS

This patent application is the U.S. national phase of International Patent Application No. PCT/JP2017/045805, filed Dec. 20, 2017, which claims the benefit of Japanese Patent Application No. 2016-246115, filed on Dec. 20, 2016, which are incorporated by reference in their entireties herein.

TECHNICAL FIELD

The present invention relates to a crystal of glutathione trisulfide dihydrate and a method for producing the same. The present invention also relates to a simple method for producing a polysulfide in an aqueous solvent using a thiosulfate.

BACKGROUND ART

Glutathione trisulfide, which is a kind of trisulfide, is known as an analogue of oxidized glutathione (Non-Patent Document 1). Glutathione trisulfide is reduced by glutathione reductase in vivo, and hydrogen sulfide is generated at that time (Non-Patent Document 2). Generated hydrogen sulfide activates γ-glutamylcysteine synthase, and the activated γ-glutamylcysteine synthase increases a glutathione level in vivo (Non-Patent Document 3).

Since glutathione has an antioxidant effect, when the glutathione level in vivo increases, it is possible to efficiently protect cells from peroxide and active oxygen species. From the above effect, in recent years, glutathione trisulfide has been increasingly expected to be an antioxidant component.

As a method for preparing glutathione trisulfide, a chemical synthesis method in which carbon disulfide is reacted with oxidized glutathione under basic conditions (Non-Patent Document 2) is known. And as a method for purifying glutathione trisulfide, a method of obtaining a glutathione trisulfide concentrate by a technique such as high speed liquid chromatography (Non-Patent Document 2) and a separation method using an ion exchange resin and a synthetic adsorption resin by a mixed bed (Non-Patent Document 4) are known. In the methods described in Non-Patent Documents 2 and 4, the synthesized and purified glutathione trisulfide was collected by freeze drying.

Like glutathione trisulfide, a compound having a structure in which a plurality of sulfur atoms are connected is referred to as polysulfide. As a method for producing polysulfide, a method for producing alkyl polysulfide has been much reported so far (Non-Patent Document 5). The alkyl polysulfide is widely used as a preliminary sulfurizing agent, a coke refining inhibitor, and a lubricating oil additive. The alkyl polysulfide is a hydrophobic compound and has extremely low solubility in water. Therefore, as a manufacturing method of alkyl polysulfide, many methods have used an organic solvent as a solvent.

RELATED ART

Non-Patent Document

Non-Patent Document 1: Biochem. Biophys. Res. Commun. 42, 730-738, 1971

Non-Patent Document 2: Biochem. Biophys. Res. Commun., 202, 1380-1386, 1994

Non-Patent Document 3: FASEB J., 18, 1165-1167, 2004

Non-Patent Document 4: J. Chromatogr., 59, 181-184, 1971

Non-Patent Document 5: David A. Atwood, M. Kamruz Zaman, "Sulfur: Organic Polysulfanes", Encyclopedia of Inorganic Chemistry, John Wiley & Sons, Ltd., 2006

DISCLOSURE OF INVENTION

Problems to be Solved by the Invention

However, the glutathione trisulfide obtained by freeze drying described in Non-Patent Documents 2 and 4 is non-crystalline, and there is no report relating to a crystal of glutathione trisulfide and a method for producing the same so far.

In addition, in the conventionally known method for producing alkyl polysulfide, an organic solvent was often used as a solvent, and hydrophilic polysulfide having low solubility in an organic solvent could not be produced efficiently. In a method for producing polysulfide using an aqueous solvent, a toxic gas such as hydrogen sulfide and chlorine sulfide were often used, or an unstable compound having a risk of generating a toxic gas was often used.

Thus, a simple method for producing polysulfide in an aqueous solvent, which does not use a toxic gas or uses a stable compound, has been demanded.

Accordingly, the present invention aims to provide a crystal of glutathione trisulfide and a method for producing the same. The present invention also aims to provide a simple method for producing polysulfide in an aqueous solvent using a thiosulfate.

Means for Solving the Problems

The present invention relates to the following (1) to (14).

(1) A crystal of glutathione trisulfide dihydrate.

(2) The crystal according to (1) above, which has peaks at diffraction angles (2θ°) of 30.5°±0.2°, preferably ±0.1°, 17.7°±0.2°, preferably ±0.1°, 17.5°±0.2°, preferably ±0.1°, and 21.2°±0.2°, preferably ±0.1° in powder X-ray diffraction.

(3) The crystal according to (2) above, which further has peaks at diffraction angles (2θ°) of 25.3°±0.2°, preferably ±0.1°, 21.5°±0.2°, preferably ±0.1°, 21.8°±0.2°, preferably ±0.1°, and 19.0°±0.2°, preferably ±0.1° in powder X-ray diffraction.

(4) The crystal according to (3) above, which further has peaks at diffraction angles (2θ°) of 19.2°±0.2°, preferably ±0.1°, 12.1°±0.2°, preferably ±0.1°, 25.0°±0.2°, preferably ±0.1°, and 20.3°±0.2°, preferably ±0.1° in powder X-ray diffraction.

(5) The crystal according to (4) above, which further has peaks at diffraction angles (2θ°) of 20.6°±0.2°, preferably ±0.1°, 29.7°±0.2°, preferably ±0.1°, 9.5°±0.2°, preferably ±0.1°, and 14.4°±0.2°, preferably ±0.1° in powder X-ray diffraction.

(6) The crystal according to (5) above, which further has peaks at diffraction angles (2θ°) of 27.3°±0.2°, preferably ±0.1°, 19.5°±0.2°, preferably ±0.1°, 16.5°±0.2°, preferably ±0.1°, and 25.8°+0.2°, preferably ±0.1° in powder X-ray diffraction.

(7) The crystal according to (6) above, which further has peaks at diffraction angles (2θ°) of 11.9°±0.2°, preferably ±0.1°, 23.2°±0.2°, preferably ±0.1°, and 30.0°±0.2°, preferably ±0.1° in powder X-ray diffraction.

(8) The crystal according to any one of (1) to (7) above, which has the following approximate unit cell parameters when measured at −173° C. in single crystal X-ray structure analysis: a=5.3777 Å; b=9.4390 Å; c=14.7822 Å; α=82.833°; β=89.101°; γ=89.392°; V=744.37 Å$^3$; Z=1, and has a space group P1.

(9) A method for producing a crystal of glutathione trisulfide dihydrate, comprising a step of precipitating a crystal of glutathione trisulfide dihydrate in an aqueous solution in which glutathione trisulfide is dissolved, and a step of collecting the precipitated crystal of glutathione trisulfide dihydrate.

(10) The production method according to (9) above, comprising a step of preparing the aqueous solution in which glutathione trisulfide is dissolved by leaving to stand or stirring an aqueous solution in which oxidized glutathione and thiosulfate are dissolved, before the step of precipitating the crystal of glutathione trisulfide dihydrate in the aqueous solution in which glutathione trisulfide is dissolved.

(11) The production method according to (9) or (10) above, wherein the step of precipitating the crystal of glutathione trisulfide dihydrate in the aqueous solution in which glutathione trisulfide is dissolved, is a step of precipitating the crystal of glutathione trisulfide dihydrate by concentrating the aqueous solution in which glutathione trisulfide is dissolved.

(12) A method for producing polysulfide represented by the following general formula (I), comprising a step of leaving to stand or stirring an aqueous solution in which a compound having a thiol group or a disulfide bond and thiosulfate are dissolved:

Formula (I)

(wherein n represents any natural number equal to or greater than 3, and R represents a composition obtained by removing a hydrogen atom from an arbitrary compound).

(13) The production method according to (12) above, wherein the compound having a thiol group or a disulfide bond is reduced glutathione or oxidized glutathione, and the polysulfide is at least one selected from glutathione trisulfide, glutathione tetrasulfide and glutathione pentasulfide.

(14) The production method according to (12) above, wherein the compound having a thiol group or a disulfide bond is N-acetyl-L-cysteine or N-acetyl-L-cysteine disulfide, and the polysulfide is at least one selected from N-acetyl-L-cystine trisulfide, N-acetyl-L-cystine tetrasulfide, N-acetyl-L-cystine pentasulfide and N-acetyl-L-cystine hexasulfide.

EMBODIMENTS FOR CARRYING OUT THE INVENTION

1. Crystal of Present Invention

The crystal of the present invention is a crystal of glutathione trisulfide dihydrate.

It can be confirmed that the crystal is a crystal of glutathione trisulfide, for example, by analysis using HPLC.

Analysis conditions in the analysis using HPLC, for example, can include the following conditions.
Column: Inertsil ODS-3 φ 3.0×150 mm 3 (manufactured by GL Sciences Inc.) Column temperature: 35° C.
Flow velocity: 0.5 mL/min
Eluent: a 3% methanol solution containing 0.2% sodium 1-heptanesulfonate and 6.8% potassium dihydrogenphosphate (adjusted to pH 3.0 with phosphoric acid)
Detector: UV detector (wavelength 210 nm)

It can be confirmed that the crystal is a crystal of glutathione trisulfide also by analysis by powder X-ray diffraction.

The analysis by powder X-ray diffraction can be performed, for example, by using a powder X-ray diffractometer (XRD) Ultima IV (manufactured by Rigaku Corporation), and using CuKα as the X-ray source, according to the attached instructions for use.

It can be confirmed that the crystal of glutathione trisulfide is a crystal of dihydrate, by Karl-Fischer method or thermogravimetric differential thermal analysis, by the fact of the moisture content in the crystal is generally 5.3±1.0 wt %, preferably 5.3±0.5 wt %, and more preferably 5.3±0.3 wt %.

The thermogravimetric differential analysis, for example, can be performed by measuring a weight change and a differential thermal from 30° C. to 200° C. (temperature change rate: 10° C./min) using EXSTAR 6000 (manufactured by Seiko Instruments Inc.), according to the attached instructions for use.

Examples of the crystal of the present invention can include a crystal having peaks at diffraction angles (2θ°) described in the following (i) in the powder X-ray diffraction using CuKα as the X-ray source, preferably a crystal having peaks at diffraction angles) (2θ° described in the following (i) and (ii), more preferably a crystal having peaks at diffraction angles (2θ°) described in the following (i) to (iii), further more preferably a crystal having peak at diffraction angles (2θ°) described in the following (i) to (iv), particularly preferably a crystal having peaks at diffraction angles (2θ°) described in the following (i) to (v), and most preferably a crystal having peaks at diffraction angles (2θ°) described in the following (i) to (vi).

(i) 30.5°±0.2°, preferably ±0.1°, 17.7°±0.2°, preferably ±0.1°, 17.5°±0.2°, preferably ±0.1°, and 21.2°±0.2°, preferably ±0.1°

(ii) 25.3°±0.2°, preferably ±0.1°, 21.5°±0.2°, preferably ±0.1°, 21.8°±0.2°, preferably ±0.1°, and 19.0°±0.2°, preferably ±0.1°

(iii) 19.2°±0.2°, preferably ±0.1°, 12.1°±0.2°, preferably ±0.1°, 25.0°±0.2°, preferably ±0.1°, and 20.3°±0.2°, preferably ±0.1°

(iv) 20.6°±0.2°, preferably ±0.1°, 29.7°±0.2°, preferably ±0.1°, 9.5°±0.2°, preferably +0.1°, and 14.4°±0.2°, preferably ±0.1°

(v) 27.3°±0.2°, preferably ±0.1°, 19.5°±0.2°, preferably +0.1°, 16.5°±0.2°, preferably ±0.1°, and 25.8°±0.2°, preferably ±0.1°

(vi) 11.9°±0.2°, preferably ±0.1°, 23.2°+0.2°, preferably ±0.1°, and 30.0°±0.2°, preferably ±0.1°

Figure 2:
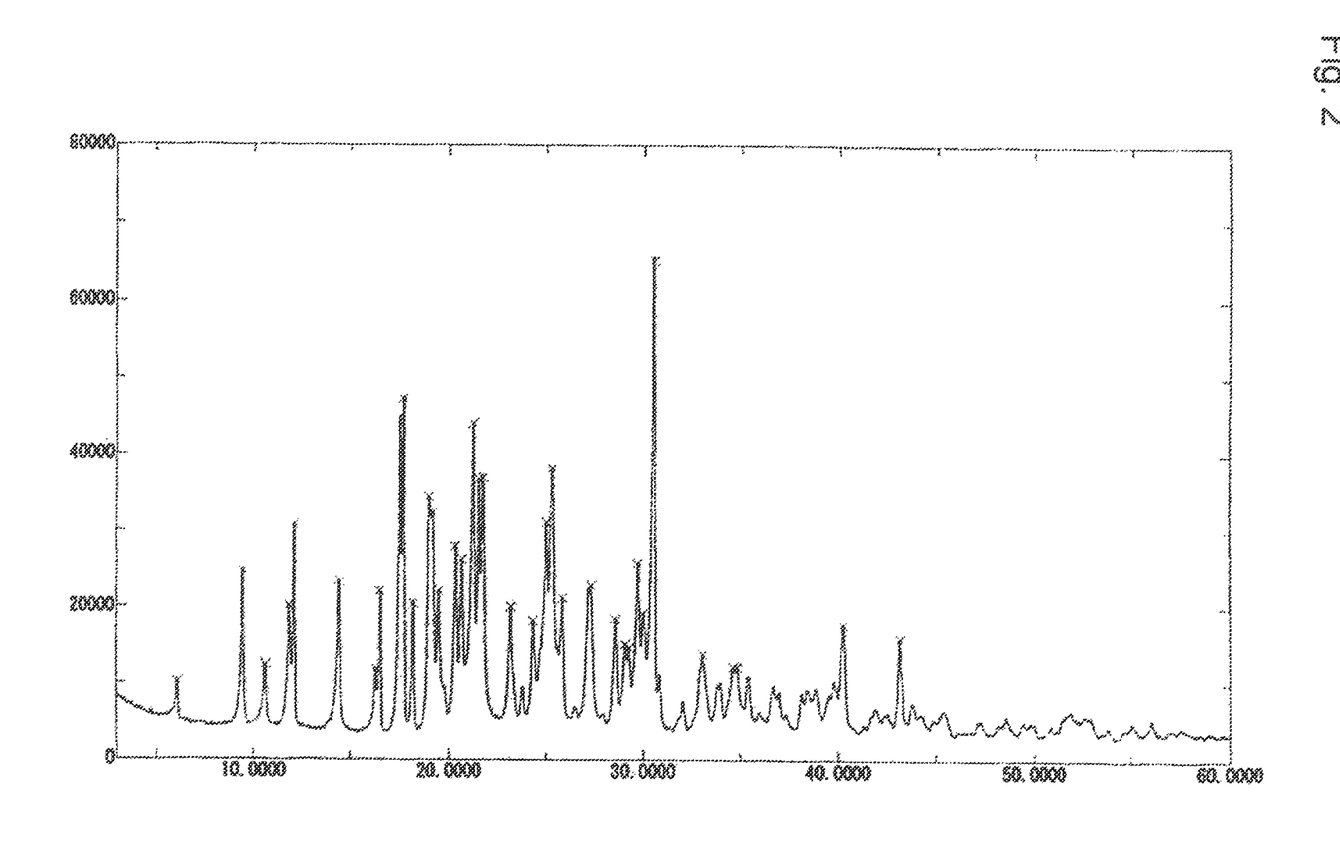
FIG. 2 represents results of powder X-ray diffraction of a crystal of glutathione trisulfide dihydrate obtained in Example 2. The vertical axis represents intensity (cps), and the horizontal axis represents a diffraction angle 2θ (°).

Specific examples of the crystal of the present invention can include a crystal of glutathione trisulfide dihydrate, in which a powder X-ray diffraction pattern using CuKα as the X-ray source is defined by a pattern shown in FIG. 2 and by values of the diffraction angle shown in Table 2, and a crystal of glutathione trisulfide dihydrate, in which a powder X-ray diffraction pattern using CuKα as the X-ray source is defined by values of the diffraction angle shown in Table 3.

Figure 3:
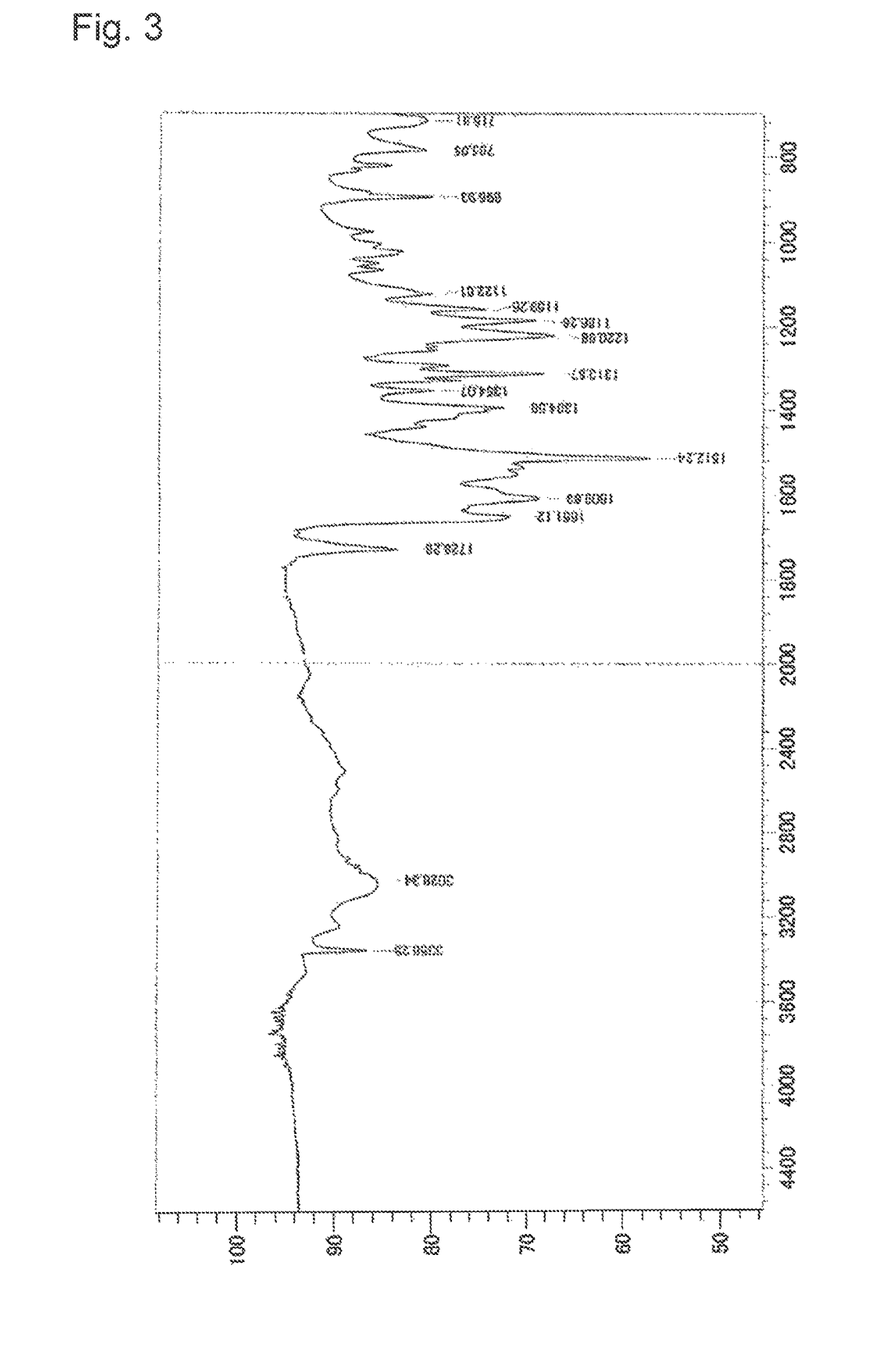
FIG. 3 represents results of infrared spectroscopy (IR) analysis of the crystal of glutathione trisulfide dihydrate obtained in Example 2. The vertical axis represents light transmittance (% T), and the horizontal axis represents a wave number (1/cm).

In addition, when provided for infrared spectroscopy (IR) analysis, the crystal of glutathione trisulfide dihydrate showing the infrared absorption spectrum shown in FIG. 3 can also be included as a specific example of the crystal of the present invention.

Infrared spectroscopy (IR) analysis, for example, can be performed using FTIR-8400 type (manufactured by Shimadzu Corporation) according to the attached instructions for use.

In addition, for example, when measured in single crystal X-ray structure analysis at about −173° C., the crystal of glutathione trisulfide dihydrate having unit cell dimensions: $a=5.3777$ Å; $b=9.4390$ Å; $c=14.7822$ Å; $\alpha=82.833°$; $\beta=89.101°$; $\gamma=89.392°$; $V=744.37$ Å$^3$; $Z=1$, and having a space group P1, can also be included as an example of the crystal of the present invention.

More specific examples can include a crystal of glutathione trisulfide dihydrate showing various results shown in Table 6 when the single crystal X-ray structure analysis is performed.

The single crystal X-ray structure analysis can be performed, for example, by using R-AXIS RAPD-F (manufactured by Rigaku Corporation) according to the instructions for use.

Specifically, for example, a single crystal of glutathione trisulfide dihydrate is attached to a diffractometer, and a diffraction image is measured using X-rays having a predetermined wavelength in atmosphere at room temperature or an inert gas stream at a predetermined temperature. A single-crystal structure is obtained by the structure determination by a direct method and the structure refinement by a least square method, from a combination of the plane index and the diffraction intensity calculated from the diffraction image.

2. Method for Producing Crystal of Present Invention

The method for producing the crystal of the present invention is a method for producing a crystal of glutathione trisulfide dihydrate, comprising a step of precipitating a crystal of glutathione trisulfide dihydrate in an aqueous solution in which glutathione trisulfide is dissolved, and a step of collecting the precipitated crystal of glutathione trisulfide dihydrate.

Glutathione trisulfide contained in the aqueous solution in which glutathione trisulfide is dissolved, may be produced by any production method such as a method of reacting oxidized glutathione and thiosulfate in an aqueous solution and other chemical synthesis methods, a fermentation method, an enzyme method, and an extraction method from natural matter.

When solid material to be an obstacle of crystallization is contained in the aqueous solution in which glutathione trisulfide is dissolved, the solid material can be removed using centrifugal separation, filtration, a ceramic filter, or the like.

In addition, when water-soluble impurities or salts to be an obstacle of crystallization are contained in the aqueous solution in which glutathione trisulfide is dissolved, it is possible to remove the water-soluble impurities or salts by passing through a column filled with an ion exchange resin or the like.

In addition, when hydrophobic impurities to be an obstacle of crystallization are contained in the aqueous solution in which glutathione trisulfide is dissolved, it is possible to remove the hydrophobic impurities by passing through a column filled with a synthetic adsorption resin, activated carbon, or the like.

The aqueous solution in which glutathione trisulfide is dissolved for use in the method for producing a crystal of the present invention is preferably adjusted and used so that a concentration of glutathione trisulfide is generally 0.1 g/L or more, and preferably 0.5 g/L or more.

The step of precipitating the crystal of glutathione trisulfide dihydrate in the aqueous solution can be performed, for example, by concentrating the aqueous solution, cooling the aqueous solution, adding or dropping an alcohol solution into the aqueous solution, or the like.

Further, for example, the concentrating of the aqueous solution, the cooling of the aqueous solution, the addition or dropping of the alcohol solution into the aqueous solution, and the like can also be performed in combination of one or more.

When the aqueous solution is concentrated, for example, a general concentration method such as a heating concentration method or a method of concentration under reduced pressure can be used.

Examples of a temperature of the aqueous solution in a case of heating concentration of the aqueous solution can include generally 40° C. to 80° C., preferably 40° C. to 70° C., and most preferably 40° C. to 60° C.

The time required for concentration in the case of heating concentration of the aqueous solution varies with a concentration of glutathione trisulfide in the aqueous solution and the temperature of the aqueous solution, but may be the time for the crystal of glutathione trisulfide dihydrate to precipitate in the aqueous solution. Those skilled in the art can appropriately set, for example, in a range of generally 2 to 100 hours, preferably 3 to 70 hours, and most preferably 5 to 50 hours.

Examples of a temperature of the aqueous solution when the aqueous solution is concentrated under reduced pressure can include generally 10° C. to 60° C., preferably 20° C. to 55° C., and most preferably 30° C. to 50° C.

The time required for concentration in the case of concentration under reduced pressure of the aqueous solution varies with a concentration of glutathione trisulfide in the aqueous solution and the temperature of the aqueous solution, but may be the time for the crystal of glutathione trisulfide dihydrate to precipitate in the aqueous solution. Specifically, for example, a range of generally 2 to 100 hours, preferably 3 to 70 hours, and most preferably 5 to 50 hours is preferable.

Specifically, for example, as described in Example 2 later, when an aqueous solution in which glutathione trisulfide is dissolved having a concentration of 0.56 g/L is concentrated under reduced pressure, the crystal of the present invention can be precipitated by concentration under reduced pressure at preferably 40 to 50° C., preferably for 10 hours.

The temperature of the aqueous solution and the time required for cooling of the aqueous solution in the case of cooling the aqueous solution vary with the concentration of glutathione trisulfide in the aqueous solution, but may be conditions in which the crystal of glutathione trisulfide dihydrate is precipitated in the aqueous solution. Specifically, for example, the temperature of the aqueous solution is preferably in a range of generally 0 to 15° C., preferably 0 to 10° C., and most preferably 0 to 5° C. In addition, for example, the time required for cooling is generally 6 hours to 8 days, preferably from 12 hours to 7 days, and most preferably 24 hours to 6 days.

When an alcohol solution is added or dropped into the aqueous solution, the alcohol solution may be a mixture of plural types of alcohol, or a mixture of alcohol and another organic solvent or water.

When the alcohol solution is a mixture of alcohol and water (hereinafter, also referred to as an alcohol aqueous solution), examples of alcohol can include preferably alcohols of C1 to C6, more preferably alcohols of C1 to C3, still more preferably alcohols selected from the group consisting of methanol, ethanol, n-propanol, and isopropyl alcohol, even more preferably methanol or ethanol, and most preferably methanol.

Further, when the alcohol solution is an alcohol aqueous solution, examples of a moisture content can include generally 40 wt % or less, preferably 20 wt % or less, more preferably 10 wt % or less, and most preferably 5 wt % or less.

When the alcohol solution is added or dropped into the aqueous solution, a temperature of the aqueous solution, an amount of the alcohol solution to be dropped or added, and time required for adding or dropping the alcohol solution vary with a concentration of glutathione trisulfide in the aqueous solution, but may be conditions in which the crystal of glutathione trisulfide dihydrate is precipitated in the aqueous solution. Specifically, for example, the temperature of the aqueous solution is preferably in a range of generally 0 to 40° C., preferably 0 to 35° C., and most preferably 5 to 30° C. In addition, for example, the amount of the alcohol solution to be added or dropped is preferably in a range of generally an equal amount of 0.1 to 100 times, preferably an equal amount of 0.1 to 10 times, and most preferably an equal amount of 0.1 to 3 times of the aqueous solution. In addition, for example, the time required for adding or dropping the alcohol solution is preferably in a range of generally 1 minute to 24 hours, preferably 1 minute to 10 hours, and most preferably 1 to 7 hours.

In the method for producing a crystal of the present invention, a seed crystal may be added immediately before starting the step of precipitating the crystal of glutathione trisulfide dihydrate in the aqueous solution, or before the crystal of glutathione trisulfide dihydrate is precipitated in the step of precipitating the crystal of glutathione trisulfide dihydrate in the aqueous solution.

As the seed crystal, for example, the crystal of glutathione trisulfide dihydrate obtained by the method for producing a crystal of the present invention can be used.

The seed crystal is added so that a concentration thereof in the aqueous solution is generally 0.001 to 50 g/L, preferably 0.01 to 5 g/L.

When the crystal of glutathione trisulfide dihydrate is precipitated by adding or dropping the alcohol solution in the aqueous solution, the time for adding the seed crystal can be set, for example, in a range of generally 0 to 12 hours, preferably 0 to 8 hours, and most preferably 0 to 4 hours after starting addition or dropping of the alcohol solution.

After precipitating the crystal of glutathione trisulfide dihydrate by the above method, the precipitated crystal can be aged over generally 1 to 48 hours, preferably 1 to 24 hours, and most preferably 1 to 12 hours.

Aging the crystal refers to growing the crystal by stopping the step of precipitating the crystal of glutathione trisulfide dihydrate.

Growing the crystal refers to increasing the crystal starting from the precipitated crystal.

Aging of the crystal is mainly performed for growing the crystal, but a new crystal may be precipitated simultaneously with the growth of the crystal.

Stopping the step of precipitating the crystal of glutathione trisulfide dihydrate, for example, refers to stopping addition or dropping of the alcohol solution when the crystal of glutathione trisulfide dihydrate is precipitated by adding or dropping the alcohol solution in the aqueous solution.

After the crystal is aged, the step of precipitating the crystal of glutathione trisulfide dihydrate may be resumed.

In the step of collecting the crystal of glutathione trisulfide dihydrate, for example, filtration, pressure filtration, suction filtration, centrifugal separation, and the like can be performed. Further, in order to reduce adhesion of mother liquor to the crystal and improve quality of the crystal, the crystal can be appropriately washed after collecting the crystal.

As a solution used for crystal washing, for example, a solution obtained by mixing one or more kinds selected from the group consisting of water, methanol, ethanol, acetone, n-propanol, and isopropyl alcohol at an arbitrary ratio can be used.

The crystal of the present invention can be obtained by drying a wet crystal obtained in this manner.

Drying conditions are not particularly limited as long as a form of the crystal of glutathione trisulfide dihydrate can be maintained, and for example, drying under reduced pressure, vacuum drying, fluidized bed drying, ventilation drying, and the like can be applied.

A drying temperature may be in any range as long as adhesive moisture or solution can be removed, and examples thereof can include preferably 80° C. or less, more preferably 70° C. or less, and most preferably 60° C. or less.

Examples of drying time can include preferably 1 to 60 hours, and more preferably 1 to 48 hours.

The method for producing a crystal of the present invention may comprise a step of preparing an aqueous solution in which glutathione trisulfide is dissolved by leaving to stand or stirring an aqueous solution in which oxidized glutathione and thiosulfate are dissolved, before the step of precipitating the crystal of glutathione trisulfide dihydrate in the aqueous solution in which glutathione trisulfide is dissolved.

Glutathione trisulfide can be generated by reacting oxidized glutathione and thiosulfate by leaving to stand or stirring the aqueous solution in which oxidized glutathione and thiosulfate are dissolved.

The oxidized glutathione used in the above step may be a non-crystalline amorphous form or a crystal; and when it is a crystal, it may be an anhydride or may contain hydrated water.

The thiosulfate used in the above step is not particularly limited, and examples thereof can include sodium thiosulfate and ammonium thiosulfate, preferably sodium thiosulfate.

The thiosulfate used in the above step may be anhydride or may contain hydrated water.

Examples of a concentration of oxidized glutathione in the aqueous solution in the above step can include generally 1 g/L or more, preferably 5 g/L or more, and more preferably 10 g/L or more.

Examples of a concentration of thiosulfate in the aqueous solution in the above step can include generally 0.1 g/L or more, preferably 0.5 g/L or more, and more preferably 1 g/L or more.

Examples of a temperature of the aqueous solution in the above step can include generally 5 to 40° C., and preferably 10 to 30° C.

Examples of pH of the aqueous solution in the above step can include pH of generally 2 to 4.

Examples of time for leaving to stand or stirring the aqueous solution in which oxidized glutathione and thiosulfate are dissolved, in the above step can include generally 2 to 48 hours, preferably 5 to 36 hours, and more preferably 8 to 24 hours.

When solid material to be an obstacle of crystallization is contained, when water-soluble impurities and salts to be an obstacle of crystallization are contained, and when hydrophobic impurities to be an obstacle of crystallization are contained in the aqueous solution in which glutathione trisulfide prepared by the above step is dissolved, the impurities can be removed as described above.

Specifically, for example, as described in Example 2 later, the aqueous solution in which glutathione trisulfide prepared by the method described above is dissolved is filtered to remove solid material such as sulfur, and then the filtrate is passed through a column filled with a synthetic adsorption resin, accordingly, an aqueous solution in which glutathione trisulfide having high purity is dissolved can be prepared.

A crystal of glutathione trisulfide dihydrate having high purity can be obtained by the above method.

Examples of the purity of the crystal of glutathione trisulfide dihydrate can include generally 93% or more, preferably 94% or more, more preferably 95% or more, and most preferably 96% or more.

The purity of the crystal of glutathione trisulfide dihydrate can be confirmed by, for example, analysis using HPLC in the same manner as that in the above 1.

Examples of the crystal of glutathione trisulfide dihydrate which can be produced by the above production method, for example, can include a crystal of glutathione trisulfide dihydrate in which a powder X-ray diffraction pattern using CuKα as the X-ray source is prescribed by a pattern shown in FIG. 2 and values of the diffraction angle shown in Table 2, and a crystal of glutathione trisulfide dihydrate in which a powder X-ray diffraction pattern using CuKα as the X-ray source is prescribed by values of the diffraction angle shown in Table 3.

In addition, when provided for infrared spectroscopy (IR) analysis, the crystal of glutathione trisulfide dihydrate showing the infrared absorption spectrum shown in FIG. 3 can also be included as a specific example of the crystal of glutathione trisulfide dihydrate that can be produced by the above production method.

In addition, the crystal of glutathione trisulfide dihydrate showing various results shown in Table 6 by single crystal X-ray structure analysis can also be included as a specific example of the crystal of glutathione trisulfide dihydrate that can be produced by the above production method.

3. Method for Producing Polysulfide of Present Invention

In addition, the present invention relates to a method for producing polysulfide, comprising a step of leaving to stand or stirring an aqueous solution in which a compound having a thiol group or a disulfide bond and thiosulfate are dissolved.

The polysulfide refers to a compound containing a large number of continuous sulfur atoms represented by the following general formula (I):

Formula (I)

(wherein n represents any natural number equal to or greater than 3, preferably any natural number of 3 to 10, more preferably any natural number of 3 to 6, and most preferably 3 or 4; further, R represents a composition obtained by removing a hydrogen atom from an arbitrary compound; and in R, a sulfur atom is bonded to a carbon atom of R).

Specific examples of R, for example, can include a composition ($C_{10}H_{16}N_3O_6$) obtained by removing a hydrogen atom from a thiol group of reduced glutathione, a composition ($C_5H_8NO_3$) obtained by removing a hydrogen atom from a thiol group of N-acetyl-L-cysteine, and a composition ($C_3H_6NO_2$) obtained by removing a hydrogen atom from a thiol group of L-cysteine.

In the present invention, a polysulfide is not particularly limited, but is preferably hydrophilic polysulfide.

In the present specification, the "hydrophilic polysulfide" refers to polysulfide in which a concentration of the polysulfide when the polysulfide is dissolved in water can be 0.1 g/L or more.

Specific examples of the hydrophilic polysulfide, for example, can include glutathione trisulfide ($C_{10}H_{16}N_3O_6$—$S_3$—$C_{10}H_6N_3O_6$), glutathione tetrasulfide ($C_{10}H_{16}N_3O_6$—$S_4$—$C_{10}H_{16}N_3O_6$), glutathione pentasulfide ($C_{10}H_{16}N_3O_6$—$S_5$—$C_{10}H_{16}N_3O_6$), N-acetyl-L-cysteine trisulfide ($C_5H_8NO_3$—$S_3$—$O_5H_8NO_3$), N-acetyl-L-cysteine tetrasulfide ($C_5H_8NO_3$—$S_4$—$O_5H_8NO_3$), N-acetyl-L-cysteine pentasulfide ($C_5H_8NO_3$—$S_5$—$O_5H_8NO_3$), and N-acetyl-L-cysteine hexasulfide ($C_5H_8NO_3$—$S_6$—$O_5H_8NO_3$), preferably glutathione trisulfide, N-acetyl-L-cysteine trisulfide, and N-acetyl-L-cysteine tetrasulfide.

The thiosulfate is not particularly limited, and examples thereof can include sodium thiosulfate and ammonium thiosulfate, preferably sodium thiosulfate. The thiosulfate salt may be an anhydride or may contain hydrated water.

The compound having a thiol group refers to a compound represented by the following general formula (II):

Formula (II)

(wherein, R represents a composition obtained by removing a hydrogen atom from an arbitrary compound; and, in R, a sulfur atom is bonded to a carbon atom of R).

The compound having a disulfide bond refers to a compound represented by the following general formula (III):

Formula (III)

(wherein, R represents a composition obtained by removing a hydrogen atom from an arbitrary compound; and in R, a sulfur atom is bonded to a carbon atom of R).

Specific examples of a compound having a thiol group or a disulfide bond, for example, can include preferably oxidized glutathione and reduced glutathione, and more preferably oxidized glutathione, when glutathione polysulfide, more specifically at least one selected from glutathione trisulfide, glutathione tetrasulfide, and glutathione pentasulfide, is produced as the polysulfide. When oxidized glutathione is used as the compound having a thiol group or a disulfide bond, the oxidized glutathione may be a non-crystalline amorphous form or a crystal, when it is a crystal, it may be nonhydrate or may contain hydrated water.

Further, for example, when an N-acetyl-L-cysteine polysulfide, more specifically at least one selected from N-acetyl-L-cysteine trisulfide, N-acetyl-L-cysteine tetrasulfide, N-acetyl-L-cysteine pentasulfide, and N-acetyl-L-cysteine hexasulfide, is produced as the polysulfide, the specific examples can include preferably N-acetyl-L-cysteine disulfide and N-acetyl-L-cysteine, more preferably N-acetyl-L-cysteine disulfide.

Those skilled in the art can appropriately set a concentration of the compound having a thiol group or a disulfide bond, a concentration of thiosulfate, and pH of a reaction aqueous solution in a reaction aqueous solution when the polysulfide is produced by the method of the present invention, according to the compound having a thiol group or a disulfide bond for use.

When the oxidized glutathione is used as the compound having a thiol group or a disulfide bond, examples of a concentration of the oxidized glutathione in an aqueous solution in which the compound having a thiol group or a disulfide bond and thiosulfate are dissolved can include generally 1 g/L or more, preferably 5 g/L or more, and more preferably 10 g/L or more.

When the oxidized glutathione is used as the compound having a thiol group or a disulfide bond, examples of a concentration of the thiosulfate in the aqueous solution can include generally 0.1 g/L or more, preferably 0.5 g/L or more, and more preferably 1 g/L or more.

When the oxidized glutathione is used as the compound having a thiol group or a disulfide bond, examples of the pH of the aqueous solution can generally include pH of 2 to 4.

When the N-acetyl-N-cysteine disulfide is used as the compound having a thiol group or a disulfide bond, examples of a concentration of the N-acetyl-N-cysteine disulfide in an aqueous solution in which the compound having a thiol group or a disulfide bond and thiosulfate are dissolved, can include generally 10 g/L or more, preferably 30 g/L or more, and more preferably 50 g/L or more.

When the N-acetyl-N-cysteine disulfide is used as the compound having a thiol group or a disulfide bond, examples of a concentration of the thiosulfate in the aqueous solution can include generally 1 g/L or more, preferably 5 g/L or more, and more preferably 10 g/L or more.

When the N-acetyl-N-cysteine disulfide is used as the compound having a thiol group or a disulfide bond, examples of the pH of the aqueous solution can include generally pH of 1.5 to 4.

Examples of a temperature for leaving to stand or stirring the aqueous solution in which the compound having a thiol group or a disulfide bond and the thiosulfate are dissolved can include generally 5 to 40° C., preferably 10 to 30° C.

Examples of time for leaving to stand or stirring the aqueous solution in which the compound having a thiol group or a disulfide bond and the thiosulfate are dissolved can include generally 2 to 48 hours, preferably 5 to 36 hours, and more preferably 8 to 24 hours.

By the above steps, the polysulfide can be easily produced in an aqueous solvent without using hydrogen sulfide.

When solid material is contained and when impurities other than the target polysulfide are contained in the aqueous solution in which the polysulfide prepared by the above steps is dissolved, the target polysulfide can be isolated and purified by filtration, centrifugal separation, chromatography using a synthetic adsorption resin or an ion exchange resin, and the like.

EXAMPLES

Hereinafter, Examples are shown, but the present invention is not limited to the following Examples.

Example 1

Production of Glutathione Polysulfide

Various sulfur-containing compounds and oxidized glutathione were used to study generation of glutathione polysulfide.

Oxidized glutathione (manufactured by Kyowa Hakko Bio Co., Ltd.) was dissolved in water and adjusted to 100 g/L, and sodium sulfate, sodium sulfite, sodium hydrogen sulfite, sodium thiosulfate, sulfuric acid, or sulfurous acid was added thereto so that their molar concentrations were the same as that of the oxidized glutathione, followed by stirring at room temperature for about 40 hours. A concentration of glutathione trisulfide in the solution was measured 0 hour, 16 hours, and 41 hours after start of the stirring. The concentration of glutathione trisulfide (g/L) for each elapsed time when each compound was added is shown in Table 1.

TABLE 1

| Compound | Elapsed time | | |
|---|---|---|---|
| | 0 hour | 16 hours | 41 hours |
| Sodium sulfate | 0.0 | 0.1 | 0.0 |
| Sodium sulfite | 0.0 | 0.0 | 0.0 |
| Sodium hydrogen sulfite | 0.0 | 0.1 | 0.0 |
| Sodium thiosulfate | 0.0 | 16.3 | 13.6 |
| Sulfuric acid | 0.0 | 0.1 | 0.1 |
| Sulfurous acid | 0.0 | 0.1 | 0.0 |

Unit: g/L

As shown in Table 1, glutathione trisulfide was generated in a significant amount only when sodium thiosulfate was added, and glutathione trisulfide was not generated in the other cases. Further, it was confirmed that glutathione tetrasulfide and glutathione pentasulfide in addition to glutathione trisulfide were generated in the solution as a result of liquid chromatography mass spectrometry measurement using 3200 QTRAP (manufactured by AB Sciex LLC).

Furthermore, pH and reaction efficiency of the reaction solution were studied at the time of production of glutathione trisulfide. 10 g of oxidized glutathione (manufactured by Kyowa Hakko Bio Co., Ltd.) was dissolved in 75 mL of water at 30° C. to prepare an oxidized glutathione aqueous solution. Thereafter, pH of the oxidized glutathione aqueous solution was adjusted to 3, 4, 5, 6, or 7 respectively by using 2N of sodium hydroxide (manufactured by Wako Pure Chemical Corporation), then adjusted to 100 mL by adding water.

Subsequently, 1.3 g of sodium thiosulfate (manufactured by Wako Pure Chemical Corporation) was added to each oxidized glutathione aqueous solution, and stirring was started. During the stirring, the concentration of glutathione trisulfide in each aqueous solution was measured every 24 hours. The results are shown in FIG. 1.

Figure 1:
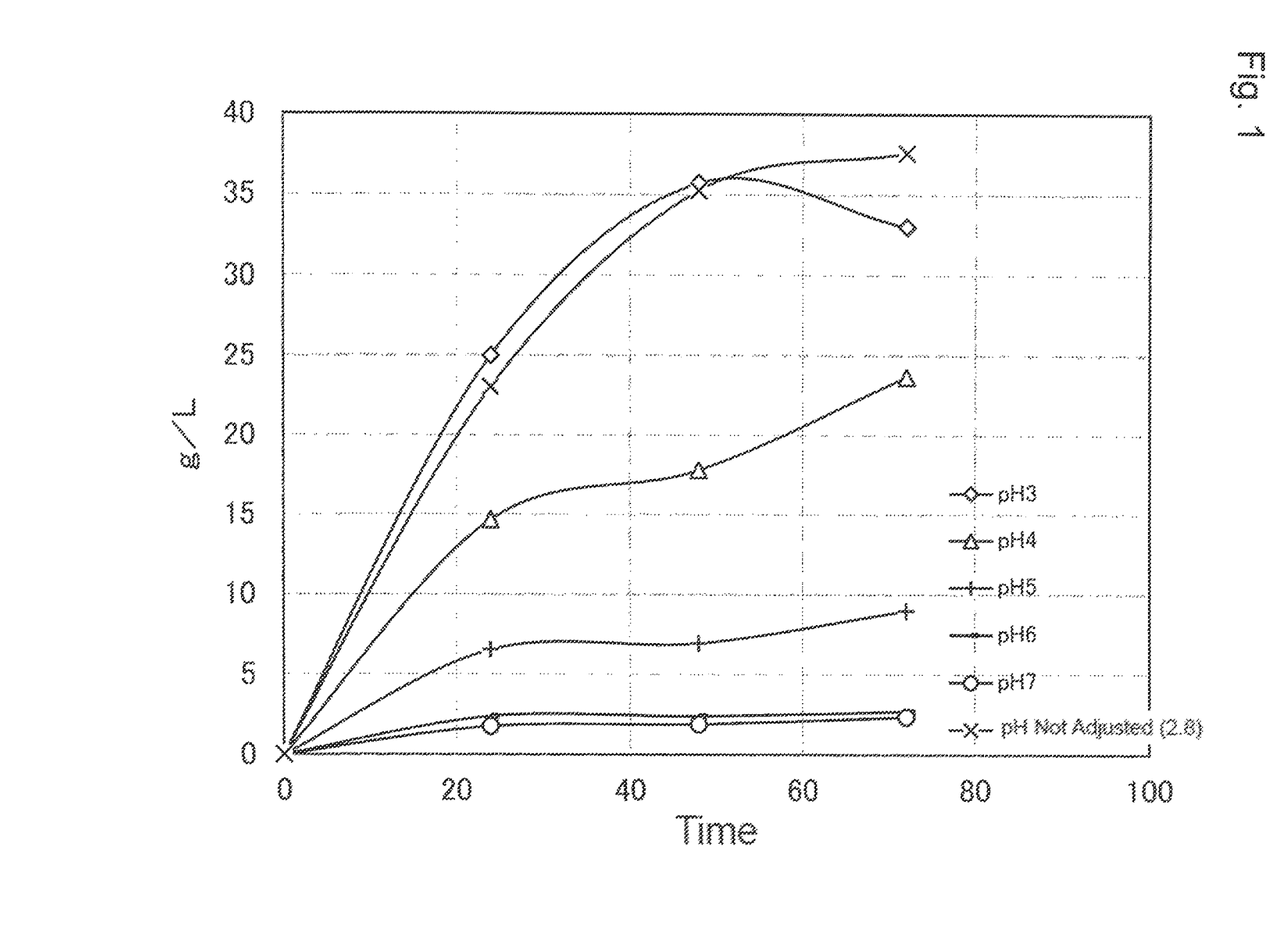
FIG. 1 represents a correlation between pH of the oxidized glutathione aqueous solution and the generation efficiency of glutathione trisulfide, obtained in Example 1. The vertical axis represents a concentration of glutathione trisulfide (g/L), and the horizontal axis represents stirring time (Time).

As shown in FIG. 1, it was found that the lower the pH of the reaction solution, the higher the concentration of glutathione trisulfide at each time, and the higher the generation efficiency of glutathione trisulfide.

Example 2

Acquisition of Crystal of Glutathione Trisulfide Dihydrate—1

To 1 L of the oxidized glutathione aqueous solution prepared by dissolving 65 g of oxidized glutathione (manufactured by Kyowa Hakko Bio Co., Ltd.) in water, 17 g of sodium thiosulfate (manufactured by Wako Pure Chemical Corporation) was added, followed by stirring at room temperature over 12 hours, to prepare 15.9 g/L of a glutathione trisulfide aqueous solution (purity: 34%).

The above aqueous solution was filtered and a precipitate such as sulfur was separated by filtration, the obtained filtrate was passed through a column filled with 500 mL of synthetic adsorption resin SP207 (manufactured by Mitsubishi Chemical Corporation). Subsequently, elution was performed using 30 L of water to obtain 25 L of 0.56 g/L of a glutathione trisulfide aqueous solution (purity: 98%).

25 L of the obtained glutathione trisulfide aqueous solution was concentrated under reduced pressure at 40 to 50° C. for 10 hours, and when it was concentrated to 500 mL, a crystal was precipitated. The precipitated crystal was separated from the aqueous solution by filtration and collected, and the crystal was dried under reduced pressure at room temperature to obtain 9.1 g of the crystal.

It was confirmed that the obtained crystal was a crystal of glutathione trisulfide by analysis using HPLC.

Further, according to thermogravimetric differential thermal analysis, it was found that the obtained crystal of glutathione trisulfide was gradually dehydrated with temperature rise (30° C. to 200° C.) to obtain an anhydride at 61° C., and that the crystal was a dihydrate from a reduced moisture weight (theoretical value: 5.3 wt %, measurement value: 5.3 wt %).

Further, according to purity measurement by HPLC, it was confirmed that the obtained crystal has glutathione trisulfide purity of 96% (area %) or more.

Table 2 shows diffraction angles of the peaks at which relative intensity ratio ($I/I_0$) is 30 or more from results of powder X-ray diffraction of the obtained crystal. In the table, "2θ" indicates a diffraction angle (2θ°), and "relative intensity" indicates a relative intensity ratio. The results of powder X-ray diffraction using CuKα as the X-ray source of the obtained crystal are shown in FIG. 2, results of infrared spectroscopy (IR) analysis are shown in FIG. 3.

TABLE 2

| 2θ | Relative strength |
| --- | --- |
| 9.5 | 38 |
| 11.9 | 31 |
| 12.1 | 48 |
| 14.4 | 36 |
| 16.5 | 34 |
| 17.5 | 68 |
| 17.7 | 73 |
| 18.2 | 32 |
| 19.0 | 53 |
| 19.2 | 50 |
| 19.5 | 35 |
| 20.3 | 43 |
| 20.6 | 41 |
| 21.2 | 68 |
| 21.5 | 57 |
| 21.8 | 57 |
| 23.2 | 31 |
| 25.0 | 48 |
| 25.3 | 59 |
| 25.8 | 33 |
| 27.3 | 36 |
| 29.7 | 40 |
| 30.0 | 30 |
| 30.5 | 100 |

Example 3

Acquisition of Crystal of Glutathione Trisulfide Dihydrate—2

30 g of oxidized glutathione (manufactured by Kyowa Hakko Bio Co., Ltd.) and 4 g of sodium thiosulfate (manufactured by Wako Pure Chemical Corporation) were dissolved in 3 L of water, the aqueous solution was stirred at 25° C. for 20 hours, and then a crystal was precipitated. The aqueous solution was filtered, and 10 g of a precipitate containing the precipitated crystal was recovered.

Subsequently, 10 g of the recovered precipitate was dissolved in 3 L of water at 60° C., the aqueous solution was filtered with a 0.45 μm of membrane filter (manufactured by Millipore Corporation), and then be obtained filtrate was concentrated under reduced pressure at 50° C. for 5 hours to 500 mL, and a crystal was precipitated.

The precipitated crystal was separated from the aqueous solution by filtration and collected, and the crystal was dried under reduced pressure at room temperature to obtain 6.5 g of the crystal.

Table 3 shows diffraction angles of peaks at which a relative intensity ratio ($I/I_0$) is 30 or more from results of powder X-ray diffraction of the obtained crystal. In the table, "2θ" indicates a diffraction angle (2θ°), and "relative intensity" indicates a relative intensity ratio.

TABLE 3

| 2θ | Relative strength |
| --- | --- |
| 9.5 | 55 |
| 11.8 | 44 |
| 12.1 | 36 |
| 14.4 | 67 |
| 16.5 | 46 |
| 17.5 | 92 |
| 17.7 | 85 |
| 18.9 | 68 |
| 19.1 | 60 |
| 19.4 | 51 |
| 20.3 | 64 |
| 20.6 | 53 |
| 21.2 | 93 |
| 21.5 | 76 |
| 21.7 | 100 |
| 23.1 | 51 |
| 24.7 | 30 |
| 25.0 | 65 |
| 25.3 | 72 |
| 25.8 | 49 |
| 27.2 | 48 |
| 27.3 | 53 |
| 28.6 | 42 |
| 29.0 | 36 |
| 29.7 | 45 |
| 29.9 | 34 |
| 30.5 | 94 |
| 40.2 | 33 |
| 40.3 | 33 |

Further, the crystal was subjected to infrared spectroscopy (IR) analysis and thermogravimetric differential analysis. Results of a powder X-ray crystal diffraction pattern, an infrared absorption spectrum, and thermogravimetric differential thermal analysis of the crystal were the same as those of the crystal obtained in Example 2, and therefore, it was found that the crystal is a crystal of glutathione trisulfide dihydrate.

Example 4

Storage Stability of Crystal of Glutathione Trisulfide Dihydrate 1 g of the crystal of glutathione trisulfide dihydrate produced in Example 2 was dissolved in water, and the volume was made up to 100 mL. The aqueous solution was filtered with a 0.45 μm of filter and then lyophilized to obtain a whitish transparent powder. When powder X-ray diffraction of the powder was measured, it was found that the powder was a non-crystalline amorphous form of glutathione trisulfide since an X-ray diffraction peak was not confirmed.

Subsequently, hygroscopicity of the obtained non-crystalline amorphous form of glutathione trisulfide and the crystal of glutathione trisulfide dihydrate produced in Example 2 was compared.

About 100 mg of each sample was weighed with a precise balance and then filled in a glass container, and after storage in THE051A (manufactured by Advantec Toyo Kaisha, Ltd.) under conditions of 40° C. and 75% relative humidity, the sample was weighed again to calculate a weight change rate. The sample weight after each elapsed time was measured with respect to 100% weight at the start of test.

The results are shown in Table 4.

TABLE 4

| Elapsed time (hour) | 0 | 0.5 | 1 | 2 | 4 |
|---|---|---|---|---|---|
| Weight of non-crystalline amorphous form (%) | 100.0 | 106.7 | 107.7 | 108.7 | 108.7 |
| Weight of crystal of dehydrate (%) | 100.0 | 100.0 | 100.0 | 100.0 | 100.0 |

As shown in Table 4, weight of the non-crystalline amorphous form increases with the elapse of time, and weight of the crystal of glutathione trisulfide dihydrate was almost not changed. From this, it was found that the crystal of glutathione trisulfide dihydrate has low hygroscopicity and excellent storage stability, as compared with the non-crystalline amorphous form.

Example 5

Impurity Selectivity of Crystal of Glutathione Trisulfide Dihydrate 3 g of the crystal of glutathione trisulfide dihydrate produced in Example 2, 0.3 g of reduced glutathione (manufactured by Kyowa Hakko Bio Co., Ltd.), and 0.3 g of oxidized glutathione (manufactured by Kyowa Hakko Bio Co., Ltd.) were dissolved in water, and the volume was made up to 100 mL. The aqueous solution was filtered with a 0.45 μm of filter and then lyophilized to obtain a whitish transparent powder. When powder X-ray diffraction of the powder was measured, it was found that the powder was an non-crystalline amorphous form since an X-ray diffraction peak was not confirmed.

Further, 3 g of the crystal of glutathione trisulfide dihydrate produced in Example 2, 0.3 g of reduced glutathione (manufactured by Kyowa Hakko Bio Co., Ltd.), and 0.3 g of oxidized glutathione (manufactured by Kyowa Hakko Bio Co., Ltd.) were dissolved in water, and the volume was made up to 100 mL. The aqueous solution was concentrated to 100 mL at 50° C. by reducing pressure, and a slurry containing the crystal of glutathione trisulfide dihydrate was obtained. The slurry was filtered to recover the crystal of glutathione trisulfide dihydrate.

Each of the non-crystalline amorphous form and the crystal of glutathione trisulfide dihydrate obtained above was weighed 200 mg in a 100 mL of measuring flask, and then water was added to 100 mL. Subsequently, quantity of the reduced glutathione and oxidized glutathione contained in the aqueous solution was determined by analysis using HPLC, and weight (wt %) of the reduced glutathione and the oxidized glutathione with respect to weight of the glutathione trisulfide contained in the aqueous solution was calculated.

Results are shown in Table 5.

TABLE 5

|  | Reduced glutathione (wt %) | Oxidized glutathione (wt %) |
|---|---|---|
| Non-crystalline amorphous form | 12.6 | 28.3 |
| Crystal of dihydrate | 0.9 | 7.9 |

As shown in Table 5, the reduced glutathione and the oxidized glutathione contained in the crystal of glutathione trisulfide dihydrate were less than the non-crystalline amorphous form. From this, it was found that impurities can be efficiently removed from glutathione trisulfide by crystallization into the crystal of dihydrate.

Example 6

Single Crystal X-ray Structure Analysis of Glutathione Trisulfide Dihydrate

In order to determine the crystal structure, the crystal of glutathione trisulfide dihydrate obtained in Example 2 was subjected to single crystal X-ray diffraction (SXRD) at −173° C. using a measurement device (single crystal X-ray structure analyzer SuperNova manufactured by Agilent Technologies).

First, single crystals of the glutathione trisulfide dihydrate were installed in a diffractometer, and the diffraction image was measured in a room temperature atmosphere or under a stream of an inert gas of a predetermined temperature, using X-rays of a predetermined wavelength. Next, a single crystal structure was obtained by the structure determination by a direct method and the structure refinement by a least square method [Acta Cryst. A64, 112 (2008)], from a combination of the plane index and the diffraction intensity calculated from the diffraction image. The results were summarized in Table 6.

TABLE 6

| Crystal data | |
|---|---|
| Chemical Formula | $C_{20}H_{36}N_6O_{14}S_3$ |
| $M_r$ | 680.72 |
| Crystal System, space group | Triclinic, P1 |
| Temperature (K) | 300 |
| a, b, c (Å) | 5.3777(3), 9.4390(5), 14.7822(8) |
| α, β, γ (°) | 82.833(6), 89.101(6), 89.392(6) |
| V (Å$^3$) | 744.37(7) |
| Z | 1 |
| Radiation type | Cu Kα |
| μ (mm$^{-1}$) | 2.96 |
| Crystal size (mm) | 0.120 × 0.070 × 0.040 |
| Data collection | |
| Diffractometer | Rigaku R-AXIS RAPID-F |
| Absorption correction | Numerical |
| No. of measured, independent and observed [I > 2σ(I)] reflections | 13481, 4888, 2985 |
| $R_{int}$ | 0.078 |
| (sin θ/λ)$_{max}$ (Å$^{-1}$) | 0.602 |
| Refinement | |
| R[F$^2$ > 2σ(F$^2$)], wR(F$^2$), S | 0.0902, 0.2395, 1.028 |
| No. of reflections | 4888 |
| No. of parameters | 402 |

TABLE 6-continued

| H-atom treatment | H-atom parameters constrained |
|---|---|
| $\Delta\rho_{max}, \Delta\rho_{min}$ (e Å$^{-3}$) | 0.39, −0.32 |
| Absolute structure | 2278 Friedel pairs (Flack, 1983) |
| Absolute structure parameter | 0.15(4) |

Computer programs: RAPID AUTO (Rigaku, 2015), CrystalStructure (Rigaku, 2016), SIR92(Altmare et al., 1994), SHELXL-97 (Sheldrick, 2008), Mercury (Macrae et al., 2008).
References
Flack, H. D. (1983). Acta Cryst. A39, 876-881.
Macrae, C. F., Bruno, I. J., Chisholm, J. A, Edgington, P. R., McCabe. P., Pidcock, E., Rodriguez-Monge, L., Taylor, R., van de Streek, J., Wood, P. A. (2008). J. Appl. Cryst. 41, 466-470.
Sheldrick, G. M. (2008). Acta Cryst. A64, 112-122.
Palatinus L., Chapuis G. (2007), J. Appl. Cryst. 40, 786-790.

The results of the single crystal x-ray structure analysis confirmed that the crystal was surely a crystal of the glutathione trisulfide, and was a dihydrate crystal having water molecules within the unit lattice. Further, the Flack parameter [Acta Cryst. A39, 876. (1983)] was 0.15 (4), close to zero, confirming that there was no contradiction in the absolute structure revealed by the analysis.

Example 7

Production of N-Acetyl-L-Cysteine Polysulfide—1

In 2 L of the N-acetyl-L-cysteine aqueous solution prepared by dissolving 202 g of N-acetyl-L-cysteine (manufactured by Kyowa Hakko Bio Co., Ltd.) in water, 2 mol/L of a sodium hydroxide aqueous solution (manufactured by Wako Pure Chemical Corporation) was added followed by adjusting the pH to 7.5, and then 63 mL of a hydrogen peroxide solution (manufactured by Wako Pure Chemical Corporation) was added and reacted at room temperature for 24 hours to oxidize N-acetyl-L-cysteine to N-acetyl-L-cysteine disulfide.

Subsequently, the aqueous solution was passed through a column filled with 160 mL of an H$^+$ type of strong cation exchange resin UBK16 (manufactured by Mitsubishi Chemical Corporation), and 3100 mL of 65 g/L of an N-acetyl-N-cysteine disulfide aqueous solution was obtained. To the obtained N-acetyl-L-cysteine disulfide aqueous solution, 48 g of sodium thiosulfate (manufactured by Wako Pure Chemical Corporation) was added, and the mixture was stirred at room temperature for 12 hours.

As a result of liquid chromatography mass spectrometry measurement using 3200QTRAP (manufactured by AB Sciex LLC), it was confirmed that N-acetyl-L-cysteine trisulfide, N-acetyl-L-cysteine tetrasulfide, N-acetyl-L-cysteine pentasulfide, and N-acetyl-L-cysteine hexasulfide were generated in the aqueous solution after stirring.

The aqueous solution was filtered to separate a precipitate such as sulfur by filtration, and the obtained filtrate was passed through a column filled with 160 mL of synthetic adsorption resin SP207 (manufactured by Mitsubishi Chemical Corporation). Subsequently, the column was washed in an order of 240 mL of water and 700 mL of a 5% methanol aqueous solution (manufactured by KANTO CHEMICAL CO., INC.), then elution was performed using a 10% methanol aqueous solution (manufactured by KANTO CHEMICAL CO., INC.), and 2500 mL of an aqueous solution containing N-acetyl-L-cysteine trisulfide was obtained.

All liquid components were evaporated by concentrating 2500 mL of the obtained N-acetyl-L-cysteine trisulfide aqueous solution under reduced pressure at 40 to 50° C. for 3 hours to obtain 0.2 g of a solid containing acetyl-L-cysteine trisulfide.

As a result of purity measurement by HPLC, it was confirmed that the obtained solid has purity of acetyl-L-cysteine trisulfide of 75% (area %) or more.

Example 8

Production of N-Acetyl-L-Cysteine Polysulfide—2

In 2 L of the N-acetyl-L-cysteine aqueous solution prepared by dissolving 202 g of N-acetyl-L-cysteine (manufactured by Kyowa Hakko Bio Co., Ltd.) in water, 2 mol/L of a sodium hydroxide aqueous solution (manufactured by Wako Pure Chemical Corporation) was added followed by adjusting the pH to 7.5, and then 63 mL of a hydrogen peroxide solution (manufactured by Wako Pure Chemical Corporation) was added and reacted at room temperature for 24 hours to oxidize N-acetyl-L-cysteine to N-acetyl-L-cysteine disulfide.

Subsequently, the aqueous solution was passed through a column filled with 160 mL of an H$^+$ type of strong cation exchange resin UBK16 (manufactured by Mitsubishi Chemical Corporation), and 3100 mL of 65 g/L of an N-acetyl-N-cysteine disulfide aqueous solution was obtained. To the obtained N-acetyl-L-cysteine disulfide aqueous solution, 48 g of sodium thiosulfate (manufactured by Wako Pure Chemical Corporation) was added, and the mixture was stirred at room temperature over 12 hours.

As a result of liquid chromatography mass spectrometry measurement using 3200QTRAP (manufactured by AB Sciex LLC), it was confirmed that N-acetyl-L-cysteine trisulfide, N-acetyl-L-cysteine tetrasulfide, N-acetyl-L-cysteine pentasulfide, and N-acetyl-L-cysteine hexasulfide were generated in the aqueous solution after stirring.

The aqueous solution was filtered to separate a precipitate such as sulfur by filtration, the obtained filtrate was passed through a column filled with 160 mL of synthetic adsorption resin SP207 (manufactured by Mitsubishi Chemical Corporation). Subsequently, the column was washed with 240 mL of water, 700 mL of a 5% methanol aqueous solution (manufactured by KANTO CHEMICAL CO., INC.), and 2500 mL of a 10% methanol aqueous solution (manufactured by KANTO CHEMICAL CO., INC.) in this order, then elution was performed using a 30% methanol aqueous solution (manufactured by KANTO CHEMICAL CO., INC.), and 550 mL of an aqueous solution containing N-acetyl-L-cysteine tetrasulfide was obtained.

All the liquid components were evaporated by concentrating 550 mL of the obtained N-acetyl-L-cysteine tetrasulfide aqueous solution under reduced pressure at 40 to 50° C. for 3 hours to obtain 0.2 g of a solid containing N-acetyl-L-cysteine tetrasulfide.

As a result of purity measurement by HPLC, it was confirmed that the obtained solid has purity of N-acetyl-L-cysteine tetrasulfide of 73% (area %) or more.

While the invention has been described in detail and with reference to specific embodiments thereof, it will be apparent to one skilled in the art that various changes and modifications can be made therein without departing from the spirit and scope thereof. The present application is based on Japanese Patent Application No. 2016-246115 filed on Dec. 20, 2016, the contents of which are incorporated herein by reference. Also, all references cited herein are incorporated as a whole.

INDUSTRIAL APPLICABILITY

The present invention provides a crystal of glutathione trisulfide that is useful as an antioxidant component, and a method for producing the same.

In addition, the present invention provides a simple method for producing a polysulfide in an aqueous solvent using a thiosulfate without using hydrogen sulfide.

The invention claimed is:

1. A crystal of glutathione trisulfide dihydrate, which has peaks at diffraction angles (2θ°) of 30.5°±0.2°, 17.7°±0.2°, 17.5°±0.2°, and 21.2°±0.2° in powder X-ray diffraction.

2. The crystal according to claim 1, which further has peaks at diffraction angles (2θ°) of 25.3°±0.2°, 21.5°±0.2°, 21.8°±0.2°, and 19.0°±0.2° in powder X-ray diffraction.

3. The crystal according to claim 2, which further has peaks at diffraction angles (2θ°) of 19.2°±0.2°, 12.1°±0.2°, 25.0°±0.2°, and 20.3°±0.2° in powder X-ray diffraction.

4. The crystal according to claim 3, which further has peaks at diffraction angles (2θ°) of 20.6°±0.2°, 29.7°±0.2°, 9.5°±0.2°, and 14.4°±0.2° in powder X-ray diffraction.

5. The crystal according to claim 4, which further has peaks at diffraction angles (2θ°) of 27.3°±0.2°, 19.5°±0.2°, 16.5°±0.2°, and 25.8°±0.2° in powder X-ray diffraction.

6. The crystal according to claim 5, which further has peaks at diffraction angles (2θ°) of 11.9°±0.2°, 23.2°±0.2°, and 30.0°±0.2° in powder X-ray diffraction.

7. The crystal according to claim 1, which has the following approximate unit cell parameters when measured at −173° C. in single crystal X-ray structure analysis: a=5.3777 Å; b=9.4390 Å; c=14.7822 Å; α=82.833°; β=89.101°; γ=89.392°; V=744.37 Å$^3$; Z=1, and has a space group P1.

8. A method for producing the crystal of glutathione trisulfide dihydrate according to claim 1, comprising a step of precipitating a crystal of glutathione trisulfide dihydrate in an aqueous solution in which glutathione trisulfide is dissolved, and a step of collecting the precipitated crystal of glutathione trisulfide dihydrate, wherein the aqueous solution comprises 0.1 g/L or more of the glutathione trisulfide dihydrate.

9. The production method according to claim 8, comprising a step of preparing the aqueous solution in which glutathione trisulfide is dissolved by leaving to stand or stirring an aqueous solution in which oxidized glutathione and thiosulfate are dissolved, before the step of precipitating the crystal of glutathione trisulfide dihydrate in the aqueous solution in which glutathione trisulfide is dissolved.

10. The production method according to claim 9, wherein the step of precipitating the crystal of glutathione trisulfide dihydrate in the aqueous solution in which glutathione trisulfide is dissolved is a step of precipitating the crystal of glutathione trisulfide dihydrate by concentrating the aqueous solution in which glutathione trisulfide is dissolved.

11. The production method according to claim 8, wherein the step of precipitating the crystal of glutathione trisulfide dihydrate in the aqueous solution in which glutathione trisulfide is dissolved is a step of precipitating the crystal of glutathione trisulfide dihydrate by concentrating the aqueous solution in which glutathione trisulfide is dissolved.

12. The crystal according to claim 2, which has the following approximate unit cell parameters when measured at −173° C. in single crystal X-ray structure analysis: a=5.3777 Å; b=9.4390 Å; c=14.7822 Å; α=82.833°; β=89.101°; γ=89.392°; V=744.37 Å3; Z=1, and has a space group P1.

13. The crystal according to claim 3, which has the following approximate unit cell parameters when measured at −173° C. in single crystal X-ray structure analysis: a=5.3777 Å; b=9.4390 Å; c=14.7822 Å; α=82.833°; β=89.101°; γ=89.392°; V=744.37 Å3; Z=1, and has a space group P1.

14. The crystal according to claim 4, which has the following approximate unit cell parameters when measured at −173° C. in single crystal X-ray structure analysis: a=5.3777 Å; b=9.4390 Å; c=14.7822 Å; a=82.833°; β=89.101°; γ=89.392°; V=744.37 Å3; Z=1, and has a space group P1.

15. The crystal according to claim 5, which has the following approximate unit cell parameters when measured at −173° C. in single crystal X-ray structure analysis: a=5.3777 Å; b=9.4390 Å; c=14.7822 Å; α=82.833°; β=89.101°; γ=89.392°; V=744.37 Å3; Z=1, and has a space group P1.

16. The crystal according to claim 6, which has the following approximate unit cell parameters when measured at −173° C. in single crystal X-ray structure analysis: a=5.3777 Å; b=9.4390 Å; c=14.7822 Å; a=82.833°; β=89.101°; γ=89.392°; V=744.37 Å3; Z=1, and has a space group P1.

17. A method for producing the crystal of glutathione trisulfide dihydrate according to claim 1, comprising preparing an aqueous solution in which glutathione trisulfide is dissolved by leaving to stand or stirring an aqueous solution in which oxidized glutathione and thiosulfate are dissolved, precipitating a crystal of glutathione trisulfide dihydrate in the aqueous solution in which glutathione trisulfide is dissolved, and collecting the precipitated crystal of glutathione trisulfide dihydrate.

18. The production method according to claim 17, wherein the step of precipitating the crystal of glutathione trisulfide dihydrate in the aqueous solution in which glutathione trisulfide is dissolved is a step of precipitating the crystal of glutathione trisulfide dihydrate by concentrating the aqueous solution in which glutathione trisulfide is dissolved.

* * * * *